United States Patent [19]
Sharpless et al.

[11] Patent Number: 6,008,376
[45] Date of Patent: Dec. 28, 1999

[54] AMINOHYDROXYLATION OF OLEFINS WITH TERT-ALKYL SULFONAMIDES

[75] Inventors: K. Barry Sharpless, La Jolla; Alexander V. Gontcharov, Solana Beach; Hong Liu, San Diego, all of Calif.

[73] Assignee: The Scripps Research Institute, La Jolla, Calif.

[21] Appl. No.: 09/138,303

[22] Filed: Aug. 21, 1998

[51] Int. Cl.$^6$ .................................................. C07D 203/24
[52] U.S. Cl. ............................................................ 548/965
[58] Field of Search ............................................. 548/965

[56] References Cited

PUBLICATIONS

CA70: 86837 Substituted aziridines. Relative rates . . . opening. Stephens et al. 1969.

King, et al., "tert–Butyl Cation Formation in the Hydrolysis of 2–Methyl–2–propanesulfonyl Chloride, the Simplest Tertiary Alkanesulfonyl Chloride", *J. Org. Chem.*, 60:2831–2834 (1995).

Bruncko, et al., "Allylic Amination and 1,2–Diamination with a Modified Diimidoselenium Reagent", *Angew. Chem. Int. Ed. Engl.*, 35(4):454–456 (1996).

Li, et al., "Catalytic Asymmetric Aminohydroxylation (AA) of Olefins", *Angew. Chem. Int. Ed. Engl.*, 35(4):451–454 (1996).

Rubin, et al., "A Highly Efficient Aminohydroxylation Process", *Angew. Chem. Int. Ed. Engl.*, 36(23):2637–2640 (1997).

Sun, et al., "tert–Butylsulfonyl (Bus), a New Protecting Group for Amines", *J. Org. Chem.*, 62:8604–8608 (1997).

*Primary Examiner*—Joseph K. McKane
*Attorney, Agent, or Firm*—Donald G. Lewis

[57] ABSTRACT

Tert-alkyl sulfonamides chloramine salts are used as nitrogen sources in the catalytic aminohydroxylation and/or aziridination of olefins. The tert-alkyl sulfonamides chloramine salts are close to Chloramine T with respect to their reactivity as nitrogen sources with olefins. However, unlike the tosyl sulfonyl amine group of Chloramine T, the resulting t-alkyl sulfonylamino functionalities can be easily converted to an unprotected amine under mild acidic conditions making the method a simple and cost efficient approach for producing unsubstituted hydroxy amine and/or aziridine products.

2 Claims, 5 Drawing Sheets

FIG. 1A  FIG. 1B  FIG. 1C

| Entry | Starting Alkene | Products (Ratios A : B)* A: BusHN-CR(OH)-C(O)-NR1R2  B: R-CH(OH)-CH(NHBus)-C(O)-NR1R2 | Combined Yield, % |
|---|---|---|---|
| 1 | Ph-CH=CH-C(O)-N(Me)-OMe | 3.3 : 1 | 93 |
| 2 | CH2=CH-C(O)-NMe2 | A | 84 |
| 3 | CH3CH2CH2-CH=CH-C(O)-NMe2 | 2.5 : 1 | 91 |
| 4 | CH2=C(Me)-C(O)-NEt2 | A | 90 |
| 5 | 2,6-dimethylphenyl-CH=CH-C(O)-NMe2 | 4.5 : 1 | 82 |
| 6 | 3-O2N-C6H4-CH=CH-C(O)-NMe2 | 1.5 : 1 | 94 |
| 7 | 4-MeO-C6H4-CH=CH-C(O)-morpholine | 5.0 : 1 | 65 |
| 8 | 4-Br-C6H4-CH=CH-C(O)-N(Me)-OMe | 1.8 : 1 | 81 |
| 9 | Ph-CH=CH-C(O)-morpholine | 3.1 : 1 | 70 |
| 10 | 4-Me-C6H4-CH=CH-C(O)-morpholine | 2.7 : 1 | 84 |
| 11 | Ph-CH=CH-C(O)-NH-iPr | 2.3 : 1 | 71 |

FIG. 2

| Alkene | Product | Yield (crude) |
|---|---|---|
| (trans-2-pentene) | N-Bus aziridine | 93 |
| (1-hexene) | 2-butyl N-Bus aziridine | 95 |
| (cyclopentene) | bicyclic Bus-N aziridine | 82 |
| cis-PhCH=CHMe | cis-2-Ph-3-Me N-Bus aziridine | 95 |
| trans-PhCH=CHMe | trans-2-Ph-3-Me N-Bus aziridine | 92 |
| styrene (PhCH=CH2) | 2-Ph N-Bus aziridine | 87 |
| (1,3-cyclohexadiene) | N-Bus bicyclic aziridine with alkene | 24 |
| (1,4-hexadiene) | N-Bus aziridine with pendant allyl | 65 |
| methylenecyclohexane | cyclohexenyl-CH2-NH-Bus | 24 |
| | spiro N-Bus aziridine | 49 |

FIG. 4B di-tert-octyl disulfide di-tert-tetradecyl disulfide di-tert-amyl disulfide di-tert-dodcyl disulfide

AMINOHYDROXYLATION OF OLEFINS WITH TERT-ALKYL SULFONAMIDES

GOVERNMENT RIGHTS

This invention was made with government support under Grant No. GM 28384 awarded by the National Institutes of Health and under Grant No. CHE 9531152 awarded by the National Science Foundation. The U.S. government has certain rights in the invention.

TECHNICAL FIELD

The present invention relates to tert-alkyl sulfonamide chloramine salts and the use of such salts as nitrogen sources in the catalytic aminohydroxylation and/or aziridination of olefins. After reaction with the tert-alkyl sulfonamide chloramine salt and an olefin under aminohydroxylation and/or aziridination conditions, the resulting tert-alkyl sulfonamide group can be removed from the aminohydroxylation and/or aziridination product under mild conditions to form an unsubstituted hydroxy-amine and aziridine product.

BACKGROUND

Chlorosulfonamide salts, such as Chloramines T and M, have been extensively used as nitrogen sources in both asymmetric and racemic aminohydroxylations, aziridinations and allylic aminations (Bruncko et al. *Angew. Chem., Int. Ed. Engl.* 1996, 35, 454; Li et al. *Angew. Chem., Int. Ed. Engl.* 1996, 35, 451; Rubin et al. *Angew. Chem., Int. Ed. Engl.* 1997, 36, 2637). However, despite their effectiveness in those reactions, they have one common substantial drawback. The removal of the alkyl- or arylsulfonyl group from the introduced sulfonylamino group is often very problematic and requires extremely harsh conditions.

Recently, Weinreb and co-workers published a communication of a new protective group for amine: t-butylsulfonyl substituted amines were found to be stable under a variety of conditions, however the t-BuSO$_2$-group could be easily removed under relatively mild acidic conditions (sun et al. *J. Org. Chem.* 1997, 62, 8604). However, Weinreb did not prepare the chloramine salt of t-butylsulfonamide or demonstrate that it could be employed t as a nitrogen source in aminohydroxylation and aziridination of olefins.

What is needed is a readily accessable and effective nitrogen source of the type R—N$^{(-)}$—Hal with an easily cleavable R—N bond which can be used in both catalytic aminohydroxylation and aziridination of olefins. Furthermore, what is needed is a simple and cost efficient method for producing such a nitrogen source.

SUMMARY

One aspect of the invention is directed to a process for converting an olefinic substrate to a tert-alkyl-sulfonamide substituted aziridine. During this process, a tert-alkyl-sulfonamide chloramine salt is employed as a nitrogen source in a catalytic addition reaction for converting the olefinic substrate into the tert-alkyl-sulfonamide substituted aziridine. In a preferred mode of this process, phenyltrimethylammonium tribromide is employed as the catalyst.

Another aspect of the invention is directed to a process for converting an olefinic substrate to an asymmetric α-substituted amine product. In the first step of this process, a tert-alkyl-sulfonamide chloramine salt is employed as a nitrogen source in a catalytic addition reaction for catalytically converting the olefinic substrate into a tert-alkyl-sulfonamide substituted aziridine. The tert-alkyl-sulfonamide substituted aziridine is then opened with a nucleophile for forming an α-substituted tert-alkyl-sulfonamide intermediate. Finally, the α-substituted tert-alkyl-sulfonamide intermediate is deprotected for forming the asymmetric α-substituted amine product. In a preferred mode of this process, the catalyst is phenyltrimethylammonium tribromide. In another preferred mode of this process, the α-substituted tert-alkyl-sulfonamide intermediate is deprotected using a mild acid.

Another aspect of the invention is directed to an improved process for converting an olefinic substrate to an asymmetric hydroxylamine product. The process is of a type which includes a catalytic asymmmetric aminohydroxylation step and a deprotection step. The catalytic asymmmetric aminohydroxylation step employs a nitrogen source and a hydroxyl source for transforming said olefinic substrate into an an asymmetric hydroxy-tert-alkyl-sulfonamide intermediate. The improvement is directed to the use of a tert-alkyl-sulfonamide chloramine salt as the nitrogen source during the catalytic asymmmetric aminohydroxylation step and to the hydrolyzation of the asymmetric hydroxy-tert-alkyl-sulfonamide intermediate during the deprotection step for producing the asymmetric hydroxylamine product. In a preferred mode of the process, a reaction solution is employed during catalytic asymmmetric aminohydroxylation step which includes the olefinic substrate, the nitrogen source, a hydroxyl radical source, osmium as a catalyst, and a chiral ligand for enantiomerically directing said asymmetric addition. In another preferred mode of the process, the asymmetric hydroxy-tert-alkyl-sulfonamide intermediate is hydrolyzed with mild acid during the deprotection step. A preferred mild acids include a 0.01–0.5 molar solution of triflic acid (TfOH) and a 0.01–0.5 molar solution of trifluoroacetic acid (TFA), each having an approximate PKa value in the range of 2–4.

Another aspect of the invention is directed to a tert-alkyl-sulfonamide chloramine salt employable in an aminohydroxylation reaction. The tert-alkyl-sulfonamide chloramine salt is represented by the following structure:

wherein R$_1$ is a tertiary-alkyl group. Preferred tertiary-alkyl groups include —C(CH$_3$)$_3$, —C(CH$_3$)$_2$—(CH$_2$)$_n$—(C(CH$_3$)$_3$), C(CH$_3$)$_2$—(CH$_2$)$_n$—CH$_3$, —C(CH$_3$)$_2$—(CH$_2$)$_n$—C(CH$_3$)$_2$—(CH$_2$)$_n$—C(CH$_3$)$_2$—(CH$_2$)$_n$—CH$_3$, and —C(CH$_3$)$_2$—(CH$_2$)$_n$—CH$_3$, wherein $0 \leq n \leq 8$.

Another aspect of the invention is directed to a process for synthesizing a tert-alkyl sulfonamide chloramine salt represented by the following structure:

In the first step of the process, a bis-tert-alkyl-disulfide is oxidized with an oxidizing agent for forming a tert-alkyl disulfide oxide intermediate. The bis-tert-alkyl-disulfide is represented by the following structure:

wherein R₁ is a is a tertiary-alkyl group. The tert-alkyl disulfide oxide intermediate being represented by the following structure:

Then, the above tert-alkyl disulfide oxide intermediate is chlorinated with sulfuryl chloride for forming a tert-alkyl sulfonyl chloride represented by the following structure:

Then, the above tert-alkyl sulfonyl chloride is reacted with sodium azide for forming a tert-alkyl sulfonamide represented by the following structure:

Finally, the above tert-alkyl sulfonamide is treated with a hypochlorite and sodium hydroxide for producing the tert-alkyl-sulfonamide chloramine salt.

DESCRIPTION OF FIGURES

FIG. 1 illustrates the following: (1A)represents the conventional method of synthesis of sulfonamides which includes a reaction of ammonia with sulfonyl chlorides prepared from the corresponding sulfonic acids; (1B) shows that if sodium azide (instead of hydroxylamine) provides a much more efficient way to accomplish the direct conversion of 1 to 2; the reaction is conducted in refluent acetonitrile containing small amount of water; (1C) shows that the intermediate t-butyl sulfinyl chloride can be prepared from commercially available bis-t-butyl disulfide in two steps with the indicated reaction conditions shown in the scheme.

FIG. 4 illustrates A) the deprotection of tert-butylsulfonylamides to form aminines using 0.1M TfOH/$CH_2Cl_2$, using conditions developed by Weinreb; B) general deprotection of tert-alkyl sulfonamides to amines using a mild acid such as 0.01–0.5 Molar TfOH solution (TFOH= triflic acid) or 0.01–0.5 Molar TFA solution ((TFA= trifluoroacetic acid) each having an approximate pK$_a$ value in the range of 2–4).

DETAILED DESCRIPTION OF THE INVENTION

The invention is directed to the use and synthesis of an effective nitrogen source of the type R—N$^{(-)}$—Hal with an easily cleavable R—N bond wherein R is a tertiary alkyl group. Furthermore, the invention is directed to the use of such nitrogen sources in both catalytic aminohydroxylation and aziridination of olefins.

t-Butyl sulfonamide, in particular, has been shown to be an efficient nitrogen source in aminohydroxylation and aziridination of olefins close to Chloramine T by its properties and behavior. However, unlike tosyl sulfonyl amine, the resulting t-butyl sulfonylamino functionality can be easily converted to an unprotected amine under mild acidic conditions. The synthesis of t-butyl sulfonamide has been accomplished on a multigram scale from cheap and readily available starting materials and reagents.

EXAMPLE 1

Synthesis t-Alkyl Sulfonamides and Corresponding Chloramine Salts

Figure 1A:
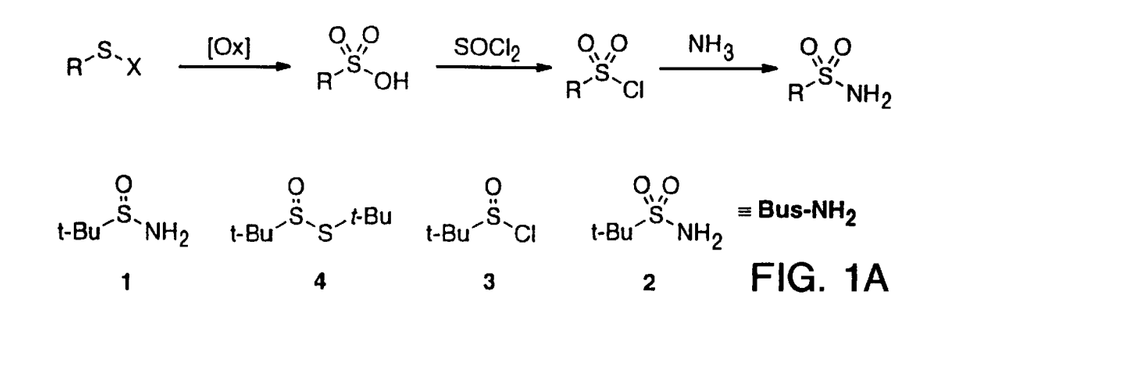

The conventional method of synthesis of sulfonamides includes a reaction of ammonia with sulfonyl chlorides, which are usually easily prepared from the corresponding sulfonic acids (FIG. 1A). This path can be efficiently used to make primary and secondary alkyl sulfonamides as well as aryl and heteroaryl sulfonamides. However, the instability of tertiary alkyl sulfonyl chlorides as well as their principally different mode of reactivity toward nucleophiles make this path inapplicable for the synthesis of tert-alkyl sulfonamides (King et al. J. Org. Chem. 1995, 60, 2831). The sulfur-nitrogen bond in this case has to be created with a lower oxidation state sulfur derivative.

Thus, tert-butylsulfonamide 1 is a fairly stable compound and can be oxidized to 2 with a variety of reagents. A number of approaches to the synthesis of 1 is documented in the literature, including reactions of t-butylsulfinyl chloride 3 with ammonia or bis-(t-butyl)disulfide oxide 4 with lithium amide. More appealing, however, was the method developed by Hovius and Engberts, who found that addition of hydroxylamine to 1 leads directly to sulfonamide 2 (Hovius et al. Tetrahedron Lett. 1972, 181). Unfortunately, the method requires use of the free base of hydroxylamine, which is very unstable.

Figure 1B:
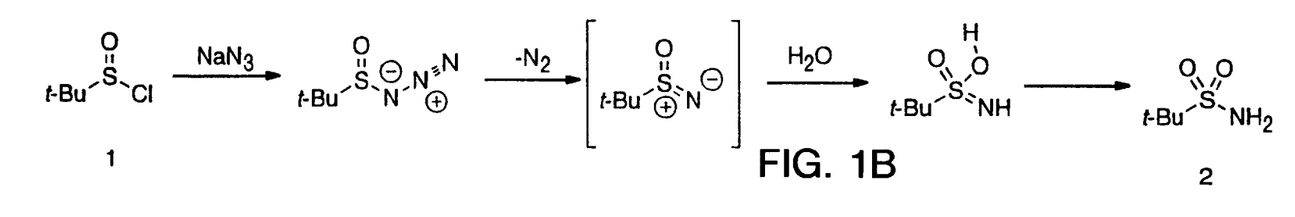
Figure 1C:
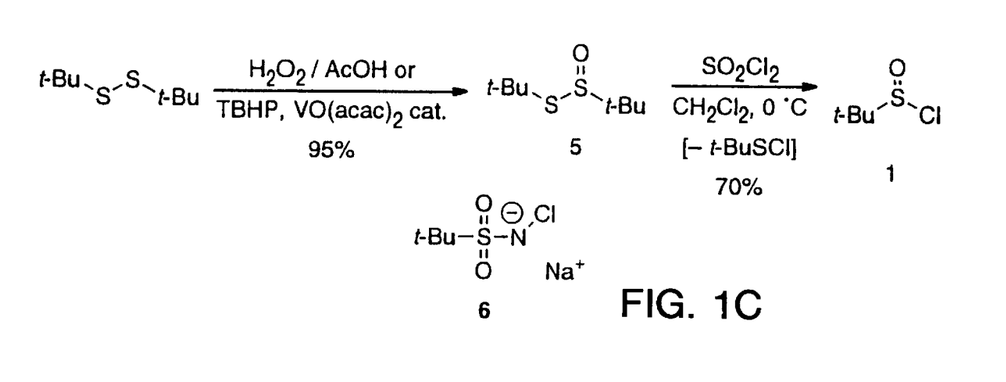

We have found that sodium azide used instead of hydroxylamine provides a much more efficient way to accomplish the direct conversion of 1 to 2. The reaction is conducted in refluent acetonitrile containing small amount of water. The initially forming sulfinyl azide is very unstable and easily loses $N_2$ (King et al. J. Org. Chem. 1995, 60, 2831). The resulting nitrene-like species is trapped by water, eventually giving sulfonamide 2 (FIG. 1B). A practical way to synthesize the intermediate t-butyl sulfinyl chloride is from commercially available bis-t-butyl disulfide in two steps as shown in FIG. 1C (Netscher et al. Synthesis 1987, 683). The whole reaction sequence was subsequently done on a multigram scale.

Figure 5A:
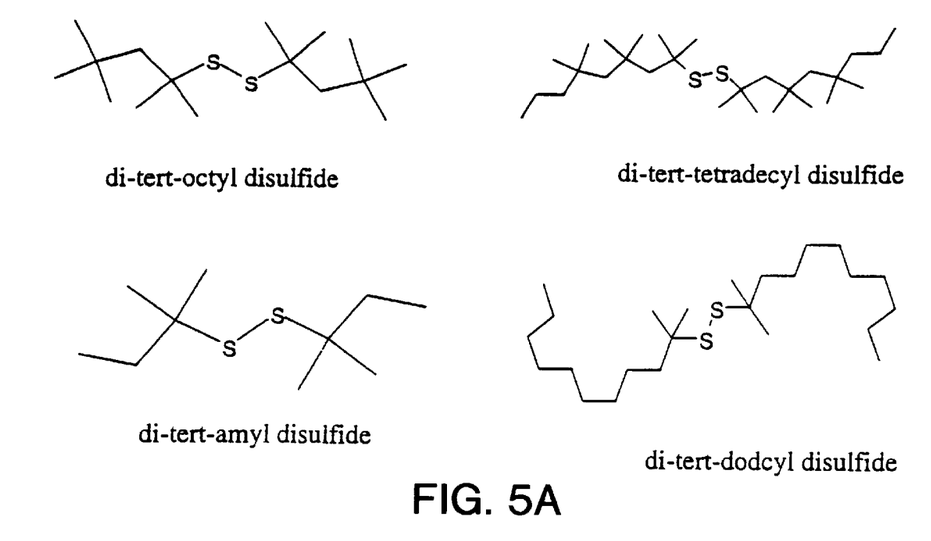
FIG. 5 illustrates various di-tert-octyl disulfides as the precursers for tert-alkyl sulfonamide chloramine salts obtained via the two step procedure as shown in FIG. 1, steps B and C.
Figure 5B:
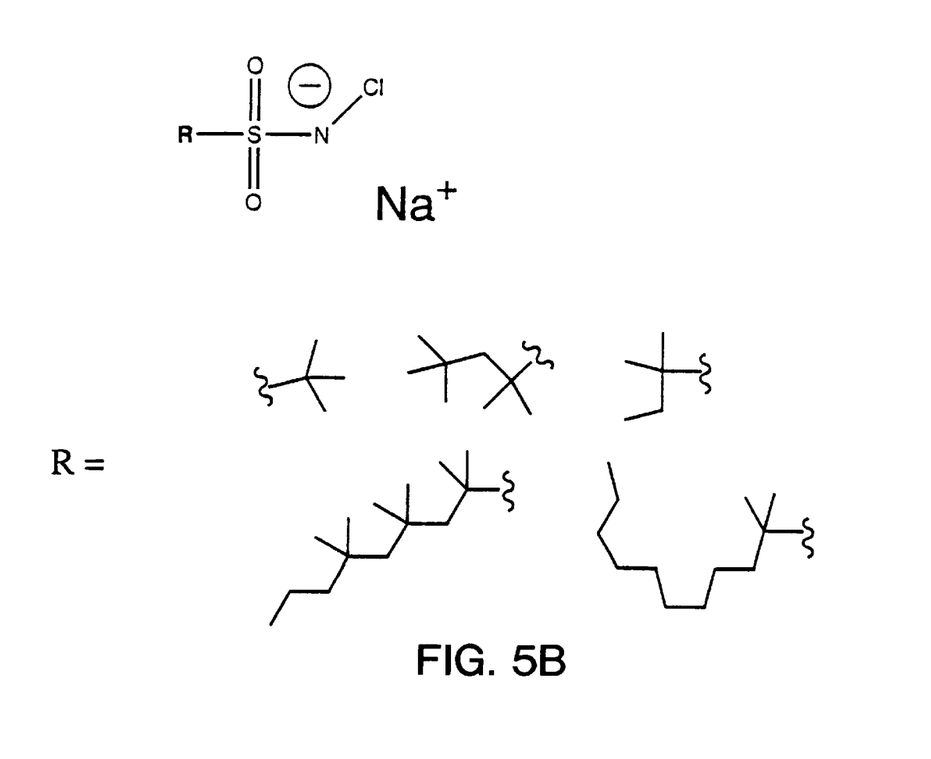

Similarly in lieu of the commercially available bis-t-butyl disulfide, other commercially available disulfides can be used to make the desired intermediate t-alkyl sulfinyl chloride in two steps as shown in FIG. 1C (scheme) and FIG. 5 (disulfides). Available disulfides include but are not restricted to di-tert-octyl disulfide, di-tert-tetradecyl-disulfide, di-tert-amyl-disulfide and di-tert-dodecyl-disulfide (the tert-alkyl sulfonamide is then synthesized exactly as for t-butyl case in two steps as shown in FIGS. 1B and 1C (Netscher et al. Synthesis 1987, 683)).

The formation of the tert-alkyl sulfonamide chloramine salt is then accomplished via standard methods known in the art and includes the treatment of the tert-alkyl-sulfonamide (eg. Bus-NH$_2$ (2)) with 1 equivalent of t-butyl hypochlorite and 1 equivalent of sodium hydroxide to give the corresponding chloramine salt (conditions are outlined in Rudolph et al. Angew. Chem., Int. Ed. Engl. 1996, 35, 281).

EXAMPLE 2

Aminohydroxylation of α,β- Unsaturated Amides Using t-Alkyl Sulfonamide Chloramine Salts Recently we reported a very efficient method of aminohydroxylation of α,β-unsaturated amides with Chloramine T as the nitrogen source and the end oxidant, and potassium osmate as the catalyst (Rubin et al. Angew. Chem., Int. Ed. Engl. 1997, 36, 2637) the reaction rates, the selectivities and the yields for this type of substrates are substantially higher compared to other substrates. In this example, we present the results of aminohydroxylation of α,β-unsaturated amides with t-butyl sulfonamido-chloride 6 as a nitrogen source under reaction conditions as reported previously by Rubin et al (other tert-alkyl sulfonamide chloramine salts can be used in lieu of t-butyl sulfonamido-chloride 6 and include the chloraminde salts of tert-octyl sulfonamide, tert-tetradecyl sulfonamide, tert-amyl sulfonamide and tert-dodecyl sulfonamide. (FIGS. 2 and 5 (b)).

Figure 2:
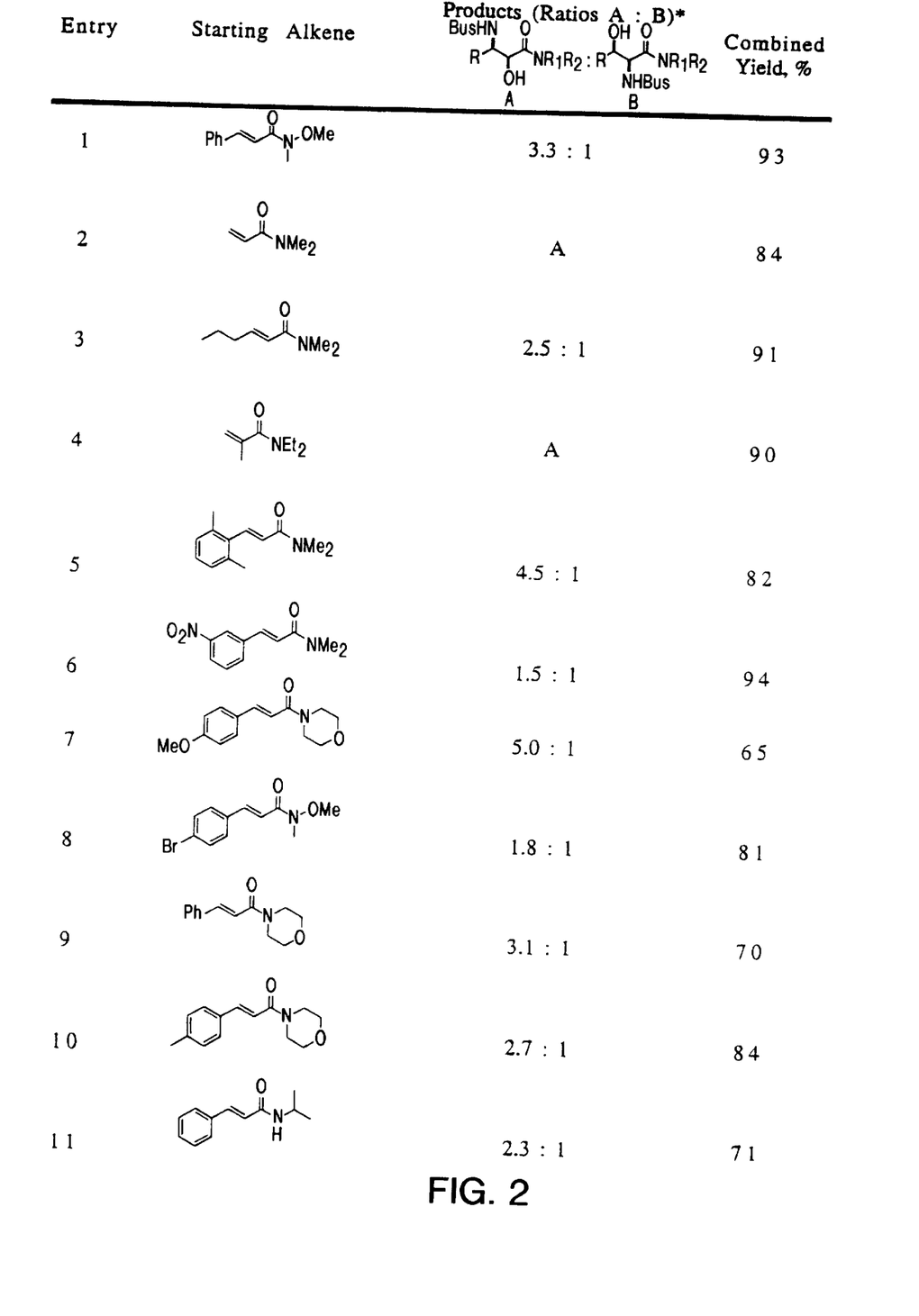
FIG. 2 illustrates the aminohydroxylation of α,β-unsaturated amides with the following reaction conditions: admixed olefin, BusNClNa (2) (1.2 eq.), $K_2OsO_2(OH)_4$ (0.5 mol%), t-BuOH-$H_2O$ 1:1, r.t and stirred for 12 hrs followed by standard work-up and purification; (*) represents ratios in isolated product.

As with previosly described Chloramine T aminoxydroxylations, this method gives high yields of aminoalcohols. In none of the cases did we observe any competitive formation of diols. The numbers in FIG. 2 show that aminohydroxylation of α,β-unsaturated amides with the new nitrogen source is as efficient as with previously reported Chloramine T. However, the possibility of easy deprotection of Bus-substituted aminoalcohols significantly increases the synthetic value of the reaction.

EXAMPLE 3

Aziridination of Olefins Using t-alkyl Sulfonamide Chloramine Salts

Aziridination of olefins with Chloramine T catalyzed by phenyltrimethylammonium tribromide (PTAB), recently discovered in our laboratory, is the second example of reaction where use of t-butyl chlorosulfonamide would make it synthetically more appealing from the point of view of the possibility of deprotection of the amino functionality, according to the method of Jeong et al. (J. Am. Chem. Soc. in press).

Aziridination is carried out in acetonitrile at room temperature with 10 mol% of PTAB. The products and the yields of aziridination of a series of alkenes is presented in FIG. 3. As for aminohydroxylation, the results closely resemble those we obtained with Chloramine T. The yields are generally high for unfunctionalized olefins. The studies are currently under way to evaluate the effect of various functionalities on the outcome of the reaction.

EXAMPLE 4

Amine Deprotection of t-butylsulfonylamides

Figure 4A:
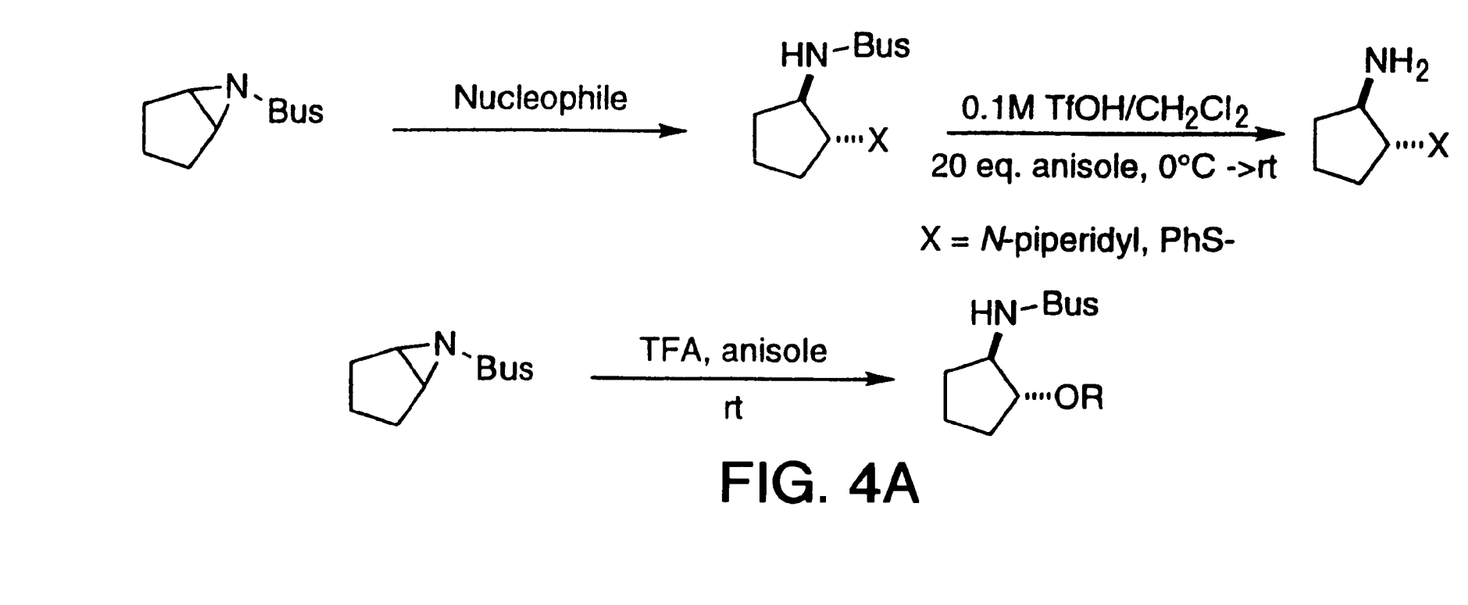
Figure 4B:
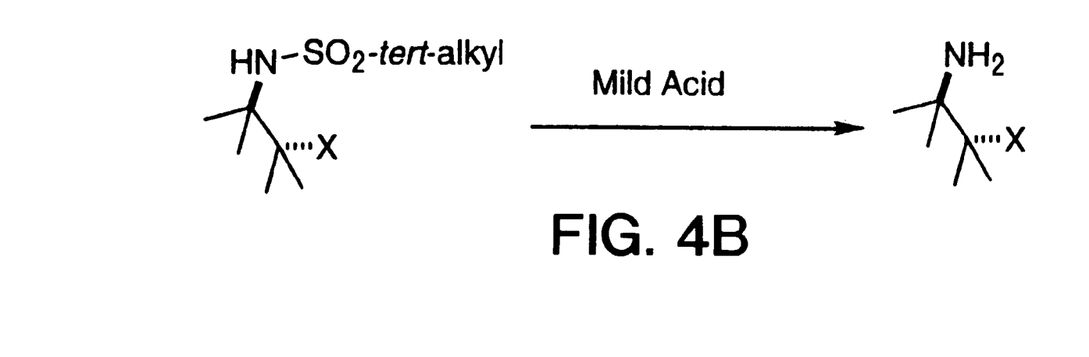

Several t-butylsulfonylamides obtained from by aziridine opening with nucleophiles were deprotected under conditions developed by Weinreb (Sun, P.; Weinreb, S. M. J. Org. Chem. 1997, 62, 8604). The Bus-protected primary amide gave high yield of the unprotected amine upon treatment with triflic acid. Attempts to deprotect the aziridine by treating it with trifluoroacetic acid were unsuccessful as aziridine opening occurred easily under those conditions (FIG. 4).

While a preferred form of the invention has been shown in the drawings and described, since variations in the preferred form will be apparent to those skilled in the art, the invention should not be construed as limited to the specific form shown and described, but instead is as set forth in the following claims.

EXPERIMENTAL PROTOCOLS

General $^1$H and $^{13}$C nmr spectra were recorded either on a Bruker AM-250, a Bruker AMX-400 or a Bruker AMX-500 spectrometer. Residual protic solvent CHCl$_3$ ($\delta_H$=7.26 ppm, $\delta_C$=77.0), d$_4$-methanol ($\delta_H$=3.30 ppm, $\delta_C$=49.0) and D$_2$O ($\delta_H$=4.80 ppm, $\delta_C$ (of CH$_3$CN)=1.7 ppm) or TMS ($\delta_H$=0.00 ppm) were used as internal reference. Coupling constants were measured in Hertz (Hz). HRMS were recorded using FAB method in a m-nitrobenzylalcohol (NBA) matrix doped with NaI or CsI. Infra-red spectra were recorded on a Perkin-Elmer FTIR 1620 spectrometer. Enantiomeric excess was determined by HPLC using a Daicel Chemical Industries CHIRALPAK AD column. Optical rotations were measured with an Optical Activity AA-1000 polarimeter. Melting points were taken on a Thomas Hoover capillary melting point apparatus and are uncorrected. Column chromatography was performed on Merck Kieselgel 60 (230–400 mesh). Analytical thin layer chromatography was performed using pre-coated glass-backed plates (Merck Kieselgel F$_{254}$) and visualized by cerium molybdophosphate or ninhydrin. Diethyl ether, tetrahydrofuran (THF) and toluene (PhCH$_3$) were distilled from sodium-benzophenone ketyl, dichloromethane (DCM) and acetonitrile from calcium hydride. Other solvents and reagents were purified by standard procedures if necessary.

It should be noted that all preferred tert-alkyl-disulfides described herein are commercially available from TCI America.

Synthesis of t-Butyl Sulfinyl Chloride as Illustrated in FIG. 1C

A mixture of t-butyl disulfide (0.5 mol), vanadyl acetylacetonate (5.0 mmol), TBHP (4.1 M solution in benzene, 10 mL; prepared as described in Sharpless, K. B.; Verhoeven, T. R. Aldrichimica Acta 1979, 12, 63; TBHP is tert-butylhydroperoxide) and benzene (250 mL) were stirred for 10 min. at 50° C. on a water bath. Then a remainder of the solution of TBHP in benzene (0.13 mol total) was added slowly so that the temperature inside the reaction flask would not rise above 70° C. After the addition was complete, the mixture was stirred at 50° C, for 1 hour (the completion of the reaction was checked by tlc) and then chilled in an ice bath. The excess of TBHP was destroyed by treatment of the mixture with a saturated aqueous solution of sodium metabisulfite (exothermic reaction!). The organic phase was separated and washed with saturated aqueous sodium bicarbonate, brine, then dried with magnesium sulfate. The crude product was isolated in 95% yield by evaporating the solvents in vacuum. The product thus obtained contained traces of unreacted disulfide as the only impurity and it was used in the subsequent step without further purification.

t-Butyl sulfinyl chloride. To a solution of t-butyldisulfide oxide (0.64 mol) in 300 mL of methylene chloride, chilled in ice, was added slowly a solution of sulfuryl chloride (0.64 mol) in 50 mL of methylene chloride. The resulting yellow mixture was stirred for 1 hour allowing it gradually reach room temperature. At this point NMR analysis showed no starting material left. The solvent and the volatile by-products of the reaction were removed in vacuum at room temperature. The product was isolated by fractional distillation of the remaining oil in vacuum (boiling range of 65–69° C. at 24 mm Hg) as a pale yellow oil. Often, however, distilled t-butylsulfonyl chloride is contaminated with some side products (most probably, sulfur chlorides), which give it deeper yellow or even orange color. The presence of these impurities did not affect the subsequent step after which they could be most conveniently removed. Synthesis of t-Butylsulfonamide (2) as Illustrated in FIG. 1B Sodium azide (16.2 g, 249 mmol) was suspended in 100 mL of acetonitrile and 10 mL of water was added to the suspension. The mixture was heated to just below the boiling point of acetonitrile, the source of heat was removed and t-butylsulfonyl chloride (20 g, 142 mmol) was added slowly while the reaction mixture was being vigorously stirred. The reaction is highly exothermic, and the addition rate was adjusted as to maintain gentle reflux of acetonitrile. After the addition was complete, the reaction mixture was allowed to cool to room temperature. Ethyl acetate (50 mL) and water (40 mL) were added and the layers were separated. The aqueous layer was extracted once with ethyl acetate, the combined organic layers were washed with water and dried with $MgSO_4$. After the solvents were evaporated in vacuo, the residue was mixed with ether and the crystals were filtered and washed with ether. The product was recrystallized from acetone to afford 14.5 g (74%) of t-butylsulfonamide as white crystals (m.p. 161–163° C., lit. 162–165° C. (Hovius et al. Tetrahedron Lett. 1972, 181).
Synthesis of Tert-alkyl Sulfonamide Chloramine Salt The formation of the tert-alkyl sulfonamide chloramine salt is accomplished via standard methods known in the art and includes the treatment of the tert-alkyl-sulfonamide (eg. Bus-$NH_2$ (2)) with 1 equivalent of t-butyl hypochlorite and 1 equivalent of sodium hydroxide to give the corresponding chloramine salt 6 (conditions are outlined in Rudolph et al. Angew. Chem., Int. Ed.
Engl. 1996, 35, 281).
General Synthesis of Tert-Alkyl Sulfinyl Chloride A mixture of the t-alkyl disulfide (0.5 mol; see above and FIG. 5 for commercially availabe disulfide reagents), vanadyl acetylacetonate (5.0 mmol), TBHP (4.1 M solution in benzene, 10 mL; prepared as described in Sharpless, K. B.; Verhoeven, T. R. Aldrichimica Acta 1979, 12, 63; TBHP is tert-butylhydroperoxide) and benzene (250 mL) were stirred for 10 min. at 50° C. on a water bath. Then a remainder of the solution of TBHP in benzene (0.13 mol total) was added slowly so that the temperature inside the reaction flask would not rise above 70° C. After the addition was complete, the mixture was stirred at 50° C. for 1 hour (the completion of the reaction was checked by tlc) and then chilled in an ice bath. The excess of TBHP was destroyed by treatment of the mixture with a saturated aqueous solution of sodium metabisulfite (exothermic reaction!). The organic phase was separated and washed with saturated aqueous sodium bicarbonate, brine, then dried with magnesium sulfate. The crude product was isolated in 95% yield by evaporating the solvents in vacuum. The product thus obtained contained traces of unreacted disulfide as the only impurity and it was used in the subsequent step without further purification. Synthesis of t-Alkyl sulfinyl chloride. To a solution of t-butyldisulfide oxide (0.64 mol) in 300 mL of methylene chloride, chilled in ice, was added slowly a solution of sulfuryl chloride (0.64 mol) in 50 mL of methylene chloride. The resulting yellow mixture was stirred for 1 hour allowing it gradually reach room temperature. At this point NMR analysis showed no starting material left. The solvent and the volatile by-products of the reaction were removed in vacuum at room temperature. The product was isolated by fractional distillation of the remaining oil in vacuum (boiling range of 65–69° C. at 24 mm Hg) as a pale yellow oil. Often, however, distilled t-alkyl sulfonyl chloride is contaminated with some side products (most probably, sulfur chlorides), which give it deeper yellow or even orange color. The presence of these impurities did not affect the subsequent step after which they could be most conveniently removed.
General Synthesis of t-Alkylsulfonamide Sodium azide (16.2 g, 249 mmol) was suspended in 100 mL of acetonitrile and 10 mL of water was added to the suspension. The mixture was heated to just below the boiling point of acetonitrile, the source of heat was removed and t-alkyl sulfonyl chloride (20 g, 142 mmol) was added slowly while the reaction mixture was being vigorously stirred. The reaction is highly exothermic, and the addition rate was adjusted as to maintain gentle reflux of acetonitrile. After the addition was complete, the reaction mixture was allowed to cool to room temperature. Ethyl acetate (50 mL) and water (40 mL) were added and the layers were separated. The aqueous layer was extracted once with ethyl acetate, the combined organic layers were washed with water and dried with $MgSO_4$. After the solvents were evaporated in vacuo, the residue was mixed with ether and the crystals were filtered and washed with ether. The product was recrystallized from acetone to afford 14.5 g (74%) of t-alkyl-sulfonamide as white crystals (m.p. 161–163° C., lit. 162–165° C. (Hovius et al. Tetrahedron Lett. 1972, 181).
General Synthesis of Tert-alkyl Sulfonamide Chloramine Salt The formation of the tert-alkyl sulfonamide chloramine salt is accomplished via standard methods known in the art and includes the treatment of the tert-alkyl-sulfonamide (with 1 equivalent of t-butyl hypochlorite and 1 equivalent of sodium hydroxide to give the corresponding chloramine salt (conditions are outlined in Rudolph et al. Angew. Chem., Int. Ed. Engl. 1996, 35, 281).
General Aminohydroxylation of α,β- Unsaturated Amides and Aziridination of Olefins as Illustrated in FIG. 2.

Aminohydroxylation with the desired tert-alkyl sulfonamide chloramine salt was carried out according to the general procedures published for Chloramine T using the desired tert-butyl-alkyl sulfonamide chloramine salt in lieu of Chloramine T (prior art: Rubin, E.; Sharpless, K. B. Angew. Chem., Int. Ed. Engl. 1997, 36, 2637; Jeong, J. U.; Tao, B.; Sagasser, I.; Henniges, H.; Sharpless, K. B. J. Am. Chem. Soc., in press).
General Procedure for Catalytic Asymmetric Aminohydroxylation in 1:1 Acetonitrile/water To a stirred solution of $(DHQ)_2$-PHAL (0.11 g, 0.14 mmol, 5 mol% or desired DHQD ligand) in 20 mL of acetonitrile and 20 mL of water, in any convenient-sized glass vessel or vial, was added desired olefin (all commercially available from Aldrich 2.8 mmol), the desired tert-alkyl sulfonamide chloramine salt (2.42 g, 8.4 mmol, 3 eq; see above for accessable salts) and $K_2OsO_2(OH)_4$ (41.6 mg, 0.112 mmol, 4 mol%). As the reaction proceeded to completion over the course of about one and half hours at room temperature, the color of the solution changed from yellow to pale green, then deep green and finally back to yellow.

After addition of aqueous sodium sulfite (1.0 g in 15 mL H$_2$O), the phases were separated, and the aqueous phase extracted with ethyl acetate (3×15 mL). The combined organic extracts were washed with brine, dried over MgSO$_4$ and the solvent concentrated to give the crude product which is purified via standard chromatographic methods.

General Procedure 2: Catalytic Asymmetric Aminohydroxylation in 1:1 Tertbutanol/water To a solution of (DHQ)$_2$-PHAL (2.20 g, 2.80 mmol, 5 mol% or desired DHQD ligand) in t-BuOH (100 mL) and water (100 ml) in 500 mL Erlenmeyer or round-bottomed flask were added in order, desired olefin (56.0 mmol), the desired tert-alkyl sulfonamide chloramine salt (48.4 g, 0.168 mol, 3.0 eq) and K$_2$OsO$_2$(OH)$_4$ (0.824 g, 2.24 mmol, 4 mol%). The reaction flask was immersed in a room-temperature water bath and the slurry stirred for 2.5 hr. Over the course of the reaction, the color changed from brown to deep green and then back to yellow as the olefin slurry became a hydroxysulfonamide slurry. The product was isolated by filtration and the crude solid was washed once with cold (ca 5° C.) 1:1 t-BuOH/H$_2$O(15 mL) to yield the product β-hydroxysulfonamide which is purified via standard chromatographic methods.

General Experimental Procedure for the Preparation of Sulfonamides (Generally Unproductive with Tertiary Alkyl Groups)

Some sulfonamides are commercially available. Others are prepared from commercially available sulfonyl chlorides: Reaction conditions: (a) NH3 (g), CH$_2$Cl$_2$, RT; (b) aqueous NH3, acetone, RT. Typical experimental procedure using gaseous ammonia: The sulfonyl chloride (1000, 10 mmol) is added slowly, in portions, to a stirred saturated solution of NH$_3$ in CH$_2$Cl$_2$ (10 mL) at room temperature (NH$_3$ (g) bubbled through the solvent beforehand). After the complete addition of 10, NH$_3$ (g) is bubbled through the the reaction for a further 30 min. The solvent is then removed under reduced pressure to afford the crude sulfonamide which is purified by recrystallyzation from either acetone/water or from ethyl acetate/hexane. Yield: 80–95%. Typical experimental procedure using aqueous ammonia: To a stirred 30% aqueous ammonia solution (40 mL), is added the sulfonyl chloride (60 mmol) slowly, in portions. After the complete addition the reaction is stirred at room temperature overnight. The reaction is then filtered to collect the crude sulfonamide which is purified by recrystallyzation from either acetone/water or from ethyl acetate/hexane. Yield: 80–90%.

Figure 3:
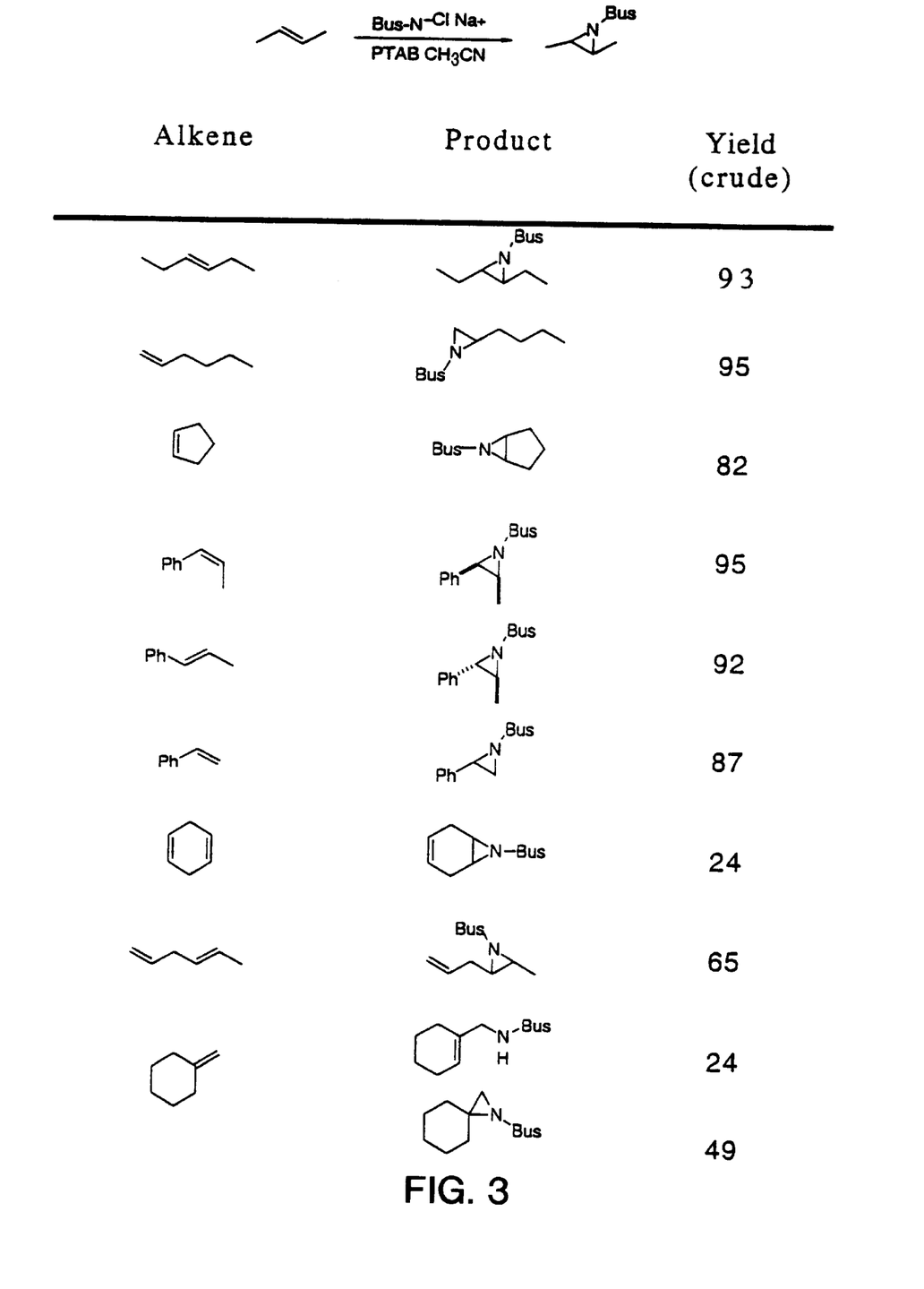
FIG. 3 illustrates the aziridination of alkenes with t-butyl chlorosulfonamide salt in the presence of PTAB as a catalyst with the following reaction conditions: admixed olefin/Bus-N⁻Cl Na+=1:1.2 mol, PTAB 10 mol%, MeCN, r.t., 10 hr.

General Procedure for the Aziridination of Olefins Using PTAB and Bus-N$^-$ClNa$^+$ as Illustrated in FIG. 3

To a mixture of trans-3-hexene (252 mg, 3 mmol 1.0 equivalents used) and anhydrous N-sodio-N-chloro tert-alkyl sulfonamide (751 mg, 3.3 mmol; see above discussion for employable tertiary salts); effective range: 1.0–2.0 equivalents; optimal concentration 1.1 equivalents) in CH3CN (15 ml, 0.2 Molar; effective range: 0.01 Molar to 1.0 Molar) was added PTAB (113 mg, 0.3 mmol; effective range: 0.05 to 0.50 equivalents; optimal concentration: 0.10 equivalents) at 25° C. (effective range 25° C. to 60° C.). After vigorous stirring for 12h (time can vary from 1h- to 24h depending on scale and substrate). The reaction mixture was worked up using standard workup conditions. A typical procedure may be carried out as follows: The reaction mixture was concentrated (about up to ⅒ volume) and filtered through a short column of silica gel (4×4 cm, 10% EtOAc in hexane). After evaporation of the solvent, the resultant solid was purified by recrystallization in hexane to give 710 mg (93%) of aziridine as colorless crystals. Modified workup: The reaction mixture was diluted with ethyl acetate (40 ml) and water (40 ml). The organic layer was separated and washed with brine (20 ml), followed by drying over MgSO4. After filtration and evaporation, the product was purified by recrystallization or column chromatography on silica gel To represent the applicability of this reaction to large scale processes, a 0.5 mol scale reaction of cyclopentene (34 g) was undertaken with Bus-N$^-$ClNa$^+$ (155 g, 0.55 mol) and 10 mol% PTAB (19 g, 0.05 mol) in CH3CN (2.5 L, therefore ~0.2 M). The aziridination product was easily isolated by crystallization of the crude reaction mixture (95 g, 80%, m.p. 71–72° C.).

General Removal of t-butylsulfonylamides Groups from AA and Aziridnation Products to Form Unprotected Hydroxyamine/aziridine Products t-alkylsulfonylamides obtained from by AA and aziridiation are deprotected under conditions developed by Weinreb (Sun, P.; Weinreb, S. M. J. Org. Chem. 1997, 62, 8604). In particular, the Bus-protected primary amide gave high yields of the unprotected amine upon treatment with 0.1 Molar triflic acid/methylene choride with 20 equivalents anisole at 0° C. to room temperature over 2–5 hr range. Attempts to deprotect the aziridine by treating it with trifluoroacetic acid were unsuccessful as aziridine opening occurred easily under those conditions as shown in FIG. 4.

While a preferred form of the invention has been shown in the drawings and described, since variations in the preferred form will be apparent to those skilled in the art, the invention should not be construed as limited to the specific form shown and described, but instead is as set forth in the following claims.

What is claimed is:

1. A process for converting an olefinic substrate to a tert-alkyl-sulfonyl substituted aziridine, the process comprising the following step:

catalyzing the addition of a tert-alkyl-sulfonyl chloramine salt as a nitrogen source to said olefinic substrate with a catalyst for producing the tert-alkyl-sulfonyl substituted aziridine.

2. A process for converting an olefinic substrate to a tert-alkyl-sulfonyl substituted aziridine as described in claim 1, wherein:

in said catalyzing step, said catalyst is phenyltrimethylammonium tribromide.

* * * * *